(12) United States Patent
Bruegger (10) Patent No.: US 6,448,024 B1
(45) Date of Patent: Sep. 10, 2002

(54) METHOD, REAGENT, CARTRIDGE, AND DEVICE FOR DETERMINING FIBRINOGEN

(75) Inventor: Berndt B. Bruegger, Camarillo, CA (US)

(73) Assignee: Roche Diagnostics Corporation, Indianapolis, IN (US)

( * ) Notice: Subject to any disclaimer, the term of this patent is extended or adjusted under 35 U.S.C. 154(b) by 37 days.

(21) Appl. No.: 09/678,950

(22) Filed: Oct. 3, 2000

(51) Int. Cl.$^7$ .............................. C12Q 1/56; C12Q 1/00
(52) U.S. Cl. ........................ 435/13; 435/4; 435/283.1
(58) Field of Search ........................... 435/13, 4, 283.1

(56) References Cited

U.S. PATENT DOCUMENTS

| | | | |
|---|---|---|---|
| 4,666,831 A | 5/1987 | Janoff et al. | 435/13 |
| 4,672,030 A | 6/1987 | Witt | 435/13 |
| 4,732,860 A | 3/1988 | Bartl et al. | 436/34 |
| 4,755,461 A | 7/1988 | Lawson et al. | 435/13 |
| 4,756,884 A | 7/1988 | Hillman et al. | 435/13 |
| 4,946,775 A | 8/1990 | Yin | 435/13 |
| 5,039,617 A | 8/1991 | McDonald et al. | 435/13 |
| 5,292,664 A | 3/1994 | Fickenscher | 435/13 |
| 5,300,779 A | 4/1994 | Hillman et al. | 436/69 |
| 5,401,663 A | 3/1995 | Yonemura | 436/69 |
| 5,443,959 A | 8/1995 | Kikuchi et al. | 435/13 |
| 5,472,852 A | 12/1995 | Smirnov et al. | 435/13 |
| 5,506,112 A | 4/1996 | Lang et al. | 435/13 |
| 5,512,304 A | 4/1996 | Barrow et al. | 435/13 |
| 5,550,028 A | 8/1996 | Lee et al. | 435/13 |
| 5,563,041 A | 10/1996 | Reers | 435/13 |
| 5,705,395 A | 1/1998 | Griffin et al. | 435/13 |
| 5,770,699 A | 6/1998 | King | 435/68.1 |
| 5,834,223 A | 11/1998 | Griffin et al. | 435/13 |

FOREIGN PATENT DOCUMENTS

| | | |
|---|---|---|
| AU | 19836/99 A | 2/2002 |
| CA | 1250213 | 2/1989 |
| CA | 2096212 | 5/1993 |
| CA | 2252983 | 6/1998 |
| EP | 0 123 883 | 11/1984 |
| EP | 0 394 070 | 10/1990 |
| EP | 570354 A1 * | 11/1993 |
| EP | 0 570 356 | 11/1993 |
| EP | 0 915 340 | 5/1999 |
| EP | 01 12 3538 | 1/2002 |
| WO | WO 96/15457 | 5/1996 |
| WO | WO 99/38997 | 1/1999 |
| WO | PCT/US00/23249 | 8/2000 |
| WO | WO 01/18551 A1 | 3/2001 |

OTHER PUBLICATIONS

Caliezi, C. et al., "Patient self–control of oral anticoagulation with CoaguChek®", *Schweizerische Medizinische Wochenschrift*, vol. 24, No. 130, XP–001022799, pp. 916–923, (Jun. 17, 2000).

Dorland's Illustrated Medical Dictionary 27$^{th}$ Ed., W. B. Saunders Company, 1988, p. 60.

(List continued on next page.)

Primary Examiner—Louise N. Leary
(74) Attorney, Agent, or Firm—Brinks, Hofer, Gilson & Lione (57) ABSTRACT

The invention is a method, reagent, test cartridge and device for the determination of fibrinogen in a sample, such as undiluted blood and blood plasma. The method utilizes a reagent comprising thrombin and a thrombin inhibitor that slows the enzymatic conversion of fibrinogen to fibrin, and thus slows clotting in samples. This is particularly useful for determining fibrinogen in undiluted blood and blood plasma. Fibrinogen assay reagents comprising at least one thrombin inhibitor and thrombin, and test cartridges containing the reagents for automated analysis of fibrinogen are disclosed, along with automated devices using said reagent and test cartridges for the devices.

57 Claims, 2 Drawing Sheets

OTHER PUBLICATIONS

Bach, R. R. "Initiation of Coagulation By Tissue Factor"; CRC Critical Reviews in Biochemistry; 1988, vol. 23, No. 4, pp. 339–368.

Dodt, J. et al., "Thrombin Inhibitors of Bloodsucking Animals", Seminars in Thrombosis and Hemostasis, 1996, vol. 22, No. 2, pp. 203–208.

Gailani, D.; Broze, Jr., G. J. "Factor XII–Independent Activation of Factor XI in Plasma: Effects of Sulfatides on Tissue Factor–Induced Coagulation"; Blood; 1993, vol. 82, No. 3, pp. 813–819.

Gomperts, E. D.; Zucker, M. L. "Heparin, Brain Thromboplastin and the Insensitivity of the Prothrombin Time to Heparin Activity"; Thrombosis Research; 1977, vol. 12, pp. 105–117.

Hattersley, P. G. "Activated Coagulation Time of Whole Blood"; JAMA; 1966, vol. 196, No. 5, pp. 150–154.

Hennekens, C. H. et al., "Current and future perspectives on antithrombotic therapy of acute myocardian infarction", European Heart Journal, 1995, vol. 16(D), pp. 2–9.

Hursting, M. J. et al., "Novastan® (Brand of Argatroban): A Small–Molecule, Direct Thrombin Inhibitor", Seminars in Thrombosis and Hemostasis, 1997, vol. 23, No. 6, pp. 503–516.

Kyogashima, M.; Onaya, J.; Hara, A.; Taketomi, T. "Contradictory Functions of Sulfatide in the Blood Coagulation System as Coagulant and Anticoagulant"; Acta Biochimica Polonica; 1998, vol. 45, No. 2, pp. 493–499.

Kyogashima, M.; Onaya, J.; Hara, A.; Taketomi, T. "Sulfatide Can Markedly Enhance Thrombogenesis in Rat Deep Vein Thrombosis Model"; Glycoconjugate Journal; 1998, vol. 15, pp. 915–922.

Lehninger; Biochemistry, $2^{nd}$ Edition; Worth Publishers, New York, 1975, pp. 287–291.

Leung, L., "Application of Combinatorial Libraries and Protein Engineering to the Discovery of Novel Anti–Thrombotic Drugs", Thrombosis and Haemostasis, 1995, vol. 74, No. 1, pp. 373–376.

Maragnore, J. M., "Pre–Clinical and Clinical Studies on Hirulog: A Potent and Specific Direct Thrombin Inhibitor", The Design of Synthetic Inhibitors of Thrombin, 1993, pp. 227–236.

Matsuo, T. et al., "Clinical Application of the Synthetic Thrombin Inhibitor, Argatroban (MD–805)", Seminars in Thrombosis and Hemostasis, 1992, vol. 18, No. 2, pp. 155–160.

Matsuo, T. et al., "Development of Argatroban, a Direct Thrombin Inhibitor, and Its Clinical Application", Seminars in Thrombosis and Hemostasis, 1997, vol. 23, No. 6, pp. 517–522.

Mungall, D. R.; Wright, J. "Summary Report: Performance Evaluation of the CoaguChek™ Plus Coagulation System for Determination of the Prothrombin Time Test"; 1995, Boehringer Mannheim Corporation, Indianapolis, pp. 1–8.

Naito, K.; Fujikawa, K. "Activation of Human Blood Coagulation Factor XI Independent of Factor XII"; The Journal of Biological Chemistry; 1991, vol. 266, No. 12, pp. 7353–7358.

Okamoto, S. et al., "Enzyme–Controlling Medicines: Introduction", Seminars in Thrombosis and Hemostasis, 1997, vol. 23, No. 6, pp. 493–501.

Paborsky, L. R.; Tate, K. M.; Harris, R. J.; Yansura, D. G.; Band, L.; McCray, G.; Gorman, C.M.; O'Brien, D. P.; Chang, J. Y.; Swartz, J. R.; Fung, V. P.; Thomas, J. N.; Vehar, G. A. "Purification of Recombinant Human Tissue Factor"; Biochemistry; 1989, vol. 28, No. 20, pp. 8072–8077.

Preissner, K. T. et al., "Thrombin Regulation by Physiological Inhibitors: The Role of Vitronectin", Seminars in Thrombosis and Hemostasis, 1996, vol. 22, No. 2, pp. 165–172.

Rehemtulla, A.; Pepe, M.; Edgington, T. S. "High Level Expression of Recombinant Human Tissue Factor in Chinese Hamster Ovary Cells as a Human Thromboplastin"; Thrombosis and Haemostasis; 1991, vol. 65, No. 5, pp. 521–527.

Sanderson, P. et al., "Thrombin Inhibitor Design", Current Medicinal Chemistry, 1998, vol. 5, No. 4, pp. 289–304.

Schousboe, I; Rasmussen, M. S. "The Effect of 2–Glycoprotein I on the Dextran Sulfate and Sulfatide Activation of the Contact System (Hageman Factor System) in the Blood Coagulation"; Int. J. Biochem.; 1988, vol. 20, No. 8, pp. 787–792.

Scott, C. F.; Colman, R. W. "Fibrinogen Blocks the Autoactivation and Thrombin–Mediated Activation of Factor XI on Dextran Sulfate"; Proc. Natl. Acad. Sci. USA; Biochemistry; 1992, vol. 89, pp. 11189–11193.

Shafer, J. A., "Cardiovascular chemotherapy: anticoagulants", Current Opinion in Chemical Biology, 1998, vol. 2, pp. 458–465.

Shimada, T.; Sugo, T.; Kato, H.; Yoshida, K.; Iwanaga, S. "Activation of Factor XII and Prekallikrein with Polysaccharide Sulfates and Sulfatides: Comparison with Kaolin–Mediated Activation"; J. Biochem; 1985, vol. 97, No. 2, pp. 429–439.

Stone, S. R. et al., "Thrombin Inhibitors as Antithrombotic Agents: The Importance of Rapid Inhibition", J. Enzyme Inhibition, 1995, vol. 9, pp. 3–15.

Stürzebecher, J. et al., "Interactions of Thrombin with Benzamidine–based Inhibitors", Biol. Chem. Hoppe–Seyler, 1992, vol. 373, pp. 491–496.

Sugidachi, A. et al., "In Vitro Effects of Aprosulate Sodium, a Novel Anticoagulant, on Platelet Activation: Possible Mechanism for Antiplatelet Action", Thrombosis and Hemostasis, 1996, vol. 76, No. 5, pp. 786–790.

Tans, G.; Griffin, J. H. "Properties of Sulfatides in Factor–XII–Dependent Contact Activation"; Blood; 1982, vol. 59, No. 1, pp. 69–75.

Tans, G.; Rosing, J.; Griffin, J. H. "Sulfatide–Dependent Autoactivation of Human Blood Coagulation Factor XII (Hageman Factor)"; The Journal of Biological Chemistry; 1983, vol. 258, No. 13, pp. 8215–8222.

Tans, G.; Griffin, J. H. "Initiation of Contact Activation by Sulfatides"; Adv. Exp. Med. Biol.; 1983, vol. 156, pp. 63–72.

Tans, G.; Verkleij, A. J.; Yu, J.; Griffin, J. H. "Sulfatide Bilayers as a Surface for Contact Activation in Human Plasma"; Biochemical and Biophysical Research Communications; 1987, vol. 149, No. 3, pp. 1002–1007.

Topol, E. J., "Evolution of Improved Antithrombotic and Antiplatelet Agents: Genesis of the Comparison of Abciximab Complications with Hirulog [and Back–Up Abciximab] Events Trial (CACHET)", The American Journal of Cardiology®, 1998, vol. 82, No. 8B, pp. 63P–68P.

White, H. D., "Clinical Trials of Direct Thrombin Inhibitors in Acute Ischaemic Syndromes", Thrombosis and Haemostasis, 1997, vol. 78, No. 1, pp. 364–366.

Abstract of: Aiyappa, P. A. "Chromogenic Substrate Spectrophotometric Assays for the Measurement of Clotting Function"; Ann. N. Y. Acad. Sci.; 1981, vol. 370, 812–821.

Abstract of Bader, R.; Mannucci, P. M.; Tripodi, A.; Hirsh, J.; Keller, F.; Solleder, E. M.; Hawkins, P.; Peng, M.; Pelzer, H.; Teijidor, L.M. et al. "Multicentric Evaluation of a New PT Reagent Based on Recombinant Human Tissue Factor and Synthetic Phospholipids"; Thromb. Haemost.; 1994, vol. 71, No. 3, pp. 292–299.

Abstract of: Hara, A.; Kutsukake, Y.; Uemura, K. I.; Taketomi, T. "Anticoagulant Activity of Sulfatide and its Anti-Thrombotic Effect in Rabbit"; J. Biochem. (Tokyo); 1993, vol. 113, No. 6, pp. 781–785.

Abstract of: Sakai, T.; Kisiel, W. "Formation of Tissue Factor Activity Following Incubation of Recombinant Human Tissue Factor Apoprotein with Plasma Lipoproteins"; Thromb. Res.; 1990, vol. 60, No. 3, pp. 213–222.

Abstract of: Scarpati, E. M.; Wen, D.; Broze, Jr., G. J.; Miletich, J. P.; Flandermeyer, R. R.; Siegel, N. R.; Sadler, J. E. "Human Tissue Factor: cDNA Sequence and Chromosome Localization of the Gene"; Biochemistry; 1987, vol. 26, No. 17, pp. 5234–5238.

"PT Test Cartridges"; Package Insert, Mannheim Boehringer Corporation, 1994.

"APTT Test Cartridges"; Package Insert, Mannheim Boehringer Corporation, 1994.

"Activated THROMBOFAX® Reagent–Optimized", Package Insert, Hemoliance.

Abstract of: JP Patent No. 10072355 A; "Influenza Virus Adsorption Inhibitor"; assigned to Snow Brand Milk Prod. Co. Ltd., Suzuki T (Suzu–I), and Suzuki Y (Suzu–I).

Abstract of: JP Patent No. 62283934 A; "Liposome Prepn. Contg. Interferon"; assigned to Vitamin Kenkyusho K (Vita–N).

Abstract of: EP Patent No. 226370 A; "Adriamycin Entrapping Liposome Prepn. For Improved Antitumor Use"; assigned to Inst. App. Biochem. (Bioc–N), Oyo Seikagaku Kenkyusho KK (Oyos–N), and Vitamin Kenkyusyo KK (Vita–N).

* cited by examiner

METHOD, REAGENT, CARTRIDGE, AND DEVICE FOR DETERMINING FIBRINOGEN

BACKGROUND OF THE INVENTION

The present invention relates to the field of determining components of biological fluids, and more particularly relates to methods, reagents, test cartridges and devices useful for determining fibrinogen in physiological samples, preferably in undiluted whole blood and undiluted blood plasma samples.

The recognition of a potential role of fibrinogen in cardiovascular disorders has increased the need for reliable and simple fibrinogen assays. Prior art methods of determining fibrinogen include clotting-time dependent fibrinogen assays that determine the coagulation time of a diluted sample and correlate the clotting time with the fibrinogen concentration in a sample wherein the coagulation time is inversely proportional to the amount of fibrinogen. In addition, total protein assays have been performed to determine the amount of protein in a clot, which is then correlated with an initial fibrinogen concentration. The first type of technique requires dilution in order to slow down the rate of coagulation to facilitate obtaining a meaningful result, while the second type of technique requires isolation of a clot from the sample, washing the clot, and determining the protein content. In view of the desire to minimize the manipulation of biological fluids, such as blood, there is a need for improved assay methods that minimize sample manipulation. Thus, it is particularly desirable to have an assay that can utilize an undiluted sample, but which avoids the problems caused by rapid clotting.

The need for improved assay methods that minimize sample manipulation is demonstrated by U.S. Pat. No. 5,292,664, to Fickenscher, which discloses a test and reagent for determining fibrinogen in undiluted plasma samples. The method of Fickenscher involves the addition of a large excess of thrombin, or a protease with analogous activity, to ensure immediate conversion of all of the fibrinogen in the sample to fibrin monomers. In a preferred embodiment of Fickensher's method, a heparin inhibitor is added to prevent inhibition of thrombin. However, the aggregation of the fibrin monomers is slowed by the addition of a fibrin aggregation inhibitor, thus slowing the formation of clots. The clotting time at a constant concentration of a fibrin aggregation inhibitor can be correlated with the fibrin concentration, and hence lead to a determination of the fibrinogen level in the original sample. Thus, Fickensher's method of inhibiting clotting promotes a first reaction in the clotting pathway, followed by inhibition of a subsequent reaction. This method requires that the sample be combined with a fibrin aggregation inhibitor prior to the addition of excess thrombin, otherwise clotting will occur too rapidly for the method to be useful.

Further information on the physiological role of fibrinogen and prior assays is abundant and readily available and known to those of skill in the art. More background information can be obtained from: National Committee for Clinical Laboratory Standards, Procedure for the Determination of Fibrinogen in Plasma; Approved Guideline. NCCLS document H30-A. (ISBN 1-56238-221-7), NCCLS, 771 East Lancaster Avenue, Villanova, Penn. 19085 (1994); U.S. Pat. No. 5,563,041; and Canadian Patent 2,252,983. All documents mentioned herein are incorporated by reference as if reproduced in full below.

There remains a need for a one-step fibrinogen assay for whole undiluted blood, and corresponding reagents and devices. The term "one-step" refers to test sample manipulation steps, such as the number of manipulations required to determine the fibrinogen in a sample. There is also a need for clotting-time dependent fibrinogen assays in which sample clotting time is less than about three hundred seconds for samples containing a wide range of fibrinogen concentrations and in which clinically significant differences in sample fibrinogen concentration correlate to reliable and readily measurable differences in clotting time. There is also a need for fibrinogen assay reagents which are stable, cost effective, readily available, can be used in dry form and can be dissolved by the sample of interest, and that provide consistent results from sample to sample. It is also desired that sample containers and other surfaces that come into contact with samples, particularly blood samples, be disposable and provide minimum opportunity for human contact with the sample. Thus, there is also a need for a cartridge useful in an automated clotting time determination device, which fulfils all or most of these needs. There is also a need for an automated device that directly reports the amount of fibrinogen in a sample.

SUMMARY OF THE INVENTION

The present invention involves a method, reagent, test cartridge, and device for determining fibrinogen in a physiological sample, such as whole blood or undiluted blood plasma. The method, reagent, test cartridge and device make use of thrombin and a thrombin inhibitor. With the thrombin and thrombin inhibitor added to it, the clotting time of a sample is measured. Since the clotting time of a blood or blood plasma sample is inversely related to its fibrinogen concentration, the clotting time can be used to determine sample fibrinogen concentration by reference to the clotting times of fibrinogen standards that have been contacted with constant amounts of reagent active ingredients.

In a preferred embodiment of the present invention, the physiological sample is undiluted, such as an undiluted whole blood sample or an undiluted blood plasma sample. Preferably, activity of added thrombin, as well as the activity of the endogenous thrombin in blood samples, is inhibited in the assay, thus slowing the rate of conversion of fibrinogen in the sample to fibrin. In a preferred embodiment, clotting time is sufficiently slow in samples containing the range of fibrinogen concentrations of clinical interest that differences in clotting time can be readily linked to different fibrinogen levels. In a preferred embodiment, an assay reagent is utilized that comprises a predetermined amount of thrombin and a thrombin inhibitor that slows but does not stop thrombin enzymatic activity with respect to the conversion of fibrinogen to fibrin.

In a preferred embodiment, a device for determining sample fibrinogen concentration is provided, comprising a cartridge incorporating a reagent of the present invention, comprising thrombin and a thrombin inhibitor. In an embodiment, a test cartridge and reagent is provided which can be utilized in a one-step assay to determine fibrinogen in an undiluted whole blood sample.

In another embodiment, a test cartridge and reagent is utilized in a two-step assay to determine fibrinogen in undiluted blood plasma; the first step being the addition of a detectable material, such as but not limited to latex particles, as a surrogate for red blood cells that would be detected in a whole blood sample, and the second step being identical to the one-step assay for determining fibrinogen in whole blood.

In a preferred embodiment, the device of the present invention comprises a processor for converting sample clotting time to the fibrinogen concentration of the sample. The device preferably includes a display or other readout device for automatically reporting the sample fibrinogen concentration to the device operator, and optionally may also provide the clotting time of the sample. In an alternative embodiment, a reagent and method is provided which can be utilized in a one-step assay using a fibrometer to determine fibrinogen in an undiluted blood plasma sample or undiluted whole blood sample, wherein the clotting time of a sample is based on the time required, after contact of the sample with the reagent, for the fibrometer probe to detect a predetermined degree of resistance to movement through the sample. The clotting time is then used to determine the amount of fibrinogen in the sample.

Thus, one embodiment of the present invention is a device for use in determining fibrinogen in a sample suspected of containing fibrinogen, comprising a vessel for contacting a sample suspected of containing fibrinogen with a reagent that causes conversion of fibrinogen to fibrin thereby causing clotting, a sensor for detecting a predetermined degree of clotting, a timer for determining the amount of time for a predetermined degree of clotting to be reached, a processor that converts clotting time to the amount of fibrinogen in a sample, and a display that can report the amount of fibrinogen in a sample. Preferably, the device further comprises a reagent that causes conversion of fibrinogen to fibrin, wherein the reagent comprises thrombin and a thrombin inhibitor. The display may be electronic or may be a printer that prints out results. The display may also report clotting time, and other parameters.

Preferred thrombin inhibitors (also referred to herein as thrombin activity modulators) for use in the invention include a sulfated polysaccharide, for example dextran sulfate; a peptide with suitable thrombin inhibiting properties, for example Gly-Pro-Ala or Gly-Gly-Arg; a xanthine, for example, caffeine; a polyanetholsulfate; a polyvinylsulfate; bis-lactobionic acid (e.g., aprosulate); a benzamidine, for example a cyclic amide of 4-amidinophenylalanine, such as Nα-(β-naphthylsulfonylglycyl)-4-amidinophenylalanine piperidide; a serine protease inhibitor such as antipain; hirudin, hirulog, bivalirudin, and argatroban. Analogs of these preferred inhibitors that perform in accordance with the present invention are also included herein.

A preferred reagent utilizes a thrombin inhibitor and thrombin at pre-optimized concentrations that can be used to determine fibrinogen in samples containing fibrinogen in concentrations found over the normal physiological range of clinical interest. Preferably, the reagent can be used to reliably determine fibrinogen concentrations in samples having between about 100 mg/dL to about 400 mg/dL fibrinogen. As used herein, the term "normal range" fibrinogen concentration refers to fibrinogen concentrations between about 100 mg/dL and about 400 mg/dL fibrinogen, while "low range" refers to fibrinogen concentrations between about 0.5 mg/dL and about 100 mg/dL fibrinogen, and "high range" refers to about 400 mg/dL to about 2,000 mg/dL fibrinogen. In an embodiment, fibrinogen concentrations ranging from about 0.5 mg/dL to about 2000 mg/dL may be determined with the assay, reagent, test cartridge and device of the present invention. Samples containing low range and high range fibrinogen concentrations can be determined by optimizing assay conditions therefore.

In another aspect, the present invention includes a novel cartridge device for use in a clotting time determination device, preferably having the capability of automatically converting the clotting time of a sample to the sample's fibrinogen concentration, as well as an indicator, electronic display or other read-out device to provide the fibrinogen concentration. Optionally, the device may provide clotting time in addition to fibrinogen concentration, thus, providing a multifunctional device that may be used in other clotting time assays.

In an embodiment, the cartridge includes a housing containing an inlet port, a chamber unit, and an exit port. The cartridge preferably further comprises a first capillary unit for independently pumping (i.e., carrying or transporting) a liquid, for example, an undiluted blood sample, from the inlet port to the chamber unit. In addition, the preferred cartridge preferably includes a second capillary unit positioned between and operatively connected to the chamber unit and the exit port for independently pumping a liquid from the chamber unit to the exit port. The inlet port, first capillary unit (if present), chamber unit, second capillary unit (if present), and exit port are present in a continuous capillary pathway.

In one embodiment, contained within the capillary pathway is a reagent comprising thrombin and a thrombin inhibitor suitable for use in the assay of the present invention. The thrombin and thrombin inhibitor reagent may be formulated in a HEPES buffer matrix. A stabilizer, such as albumin, may also be present in the reagent. In another embodiment, the cartridge contains thrombin reagent, and is utilized in the assay of the present invention by passing through the cartridge a sample containing fibrinogen and a suitable thrombin inhibitor. In an alternative embodiment, the reagent in the cartridge further comprises blood cell surrogates, for example latex particles, in the reagent chamber that mix with the sample, preferably a sample such as blood plasma or synthetic blood lacking more readily detectable particulates.

In another alternative embodiment, the reagents and assay of the present invention can be used with traditional wet chemical techniques. For example, in an embodiment, a fibrometer is used to measure clotting time of fibrinogen containing samples mixed with solubilized reagents of the present invention.

The present invention, together with attendant objects and advantages, may be better understood with reference to the detailed description below in connection with the attached Figures.

DETAILED DESCRIPTION OF THE INVENTION

Fibrinogen Determination Reagent

In a preferred embodiment, a fibrinogen determination reagent is formulated to include effective amounts of thrombin and a thrombin inhibitor, which, when an effective amount of the reagent is contacted with a sample containing fibrinogen within a range of interest, causes at least a degree of clotting to occur within a predetermined amount of time. Preferably, a predetermined degree of clotting is reached in less than 300 seconds.

In an alternative embodiment, the fibrinogen determination reagent comprises thrombin, but no thrombin inhibitor, and a thrombin inhibition reagent is provided separately for mixture with samples prior to contact with the thrombin-containing fibrinogen determination reagent.

The preferred reagent is dehydrated (i.e., substantially anhydrous) to facilitate storage and transportation, and can be readily hydrated by aqueous samples, such as blood and blood plasma. The amount of thrombin can vary in the reagent. In an embodiment, when sufficient reagent is mixed with a sample in order to cause clotting in accordance with the present invention, the sample contains between about 1 U/mL and about 100 U/mL thrombin.

Suitable thrombin can be obtained from commercial sources, such as Calbiochem. Most preferably, the thrombin is bovine or human.

Preferred thrombin inhibitors (also referred to herein as thrombin activity modulators) for use in the invention include a sulfated polysaccharide, for example dextran sulfate; a peptide with suitable thrombin inhibiting properties, for example Gly-Pro-Ala or Gly-Gly-Arg; a xanthine, for example, caffeine; a polyanetholsulfate; a polyvinylsulfate; bis-lactobionic acid (aprosulate); a benzamidine, for example a cyclic amide of 4-amidinophenylalanine such as Nα-(β-naphthylsulfonylglycyl)4-amidinophenylalanine piperidide; a serine protease inhibitor such as antipain; hirudin; hirulog; bivalirudin; and argatroban.

At present, one of the most preferred thrombin inhibitors is dextran sulfate. Suitable dextran sulfate is available commercially from numerous sources, such as Sigma and Sachibo. A preferred dextran sulfate has a molecular weight (MW) between about 5,000 Daltons (Da) and about 50,000 Da (~5000 Da$\leq$MW$\leq$~50,000 Da), with a particularly preferred dextran sulfate being one having a molecular weight of between about 5,000 Da and 10,000 Da. The amount of dextran sulfate can vary in the reagent, however, it is preferred to have sufficient reagent mixed with a sample such that the sample contains between about 0.01 mg/mL and about 25 mg/mL dextran sulfate. The reagent may be used in dry form, such as for use in a cartridge of the present invention. Herein, the amount of a particular ingredient in a "cartridge reagent" or "dried reagent" refers to the concentrations of the ingredient in the reagent solution before dehydration to form the cartridge reagent or dried reagent.

Another preferred thrombin inhibitor is bis-lactobionic acid. Even more preferably, the bis-lactobionic acid is one known as aprosulate sodium, i.e. a bis-lactobionic acid amide derivative. This compound is a synthetic polyanion with known potent anticoagulant activities. (Sugidachi A, Breiter N, Ogawa T, Asai F, Koike H, In vitro effects of aprosulate sodium, a novel anticoagulant, on platelet activation: possible mechanism for antiplatelet action. *Thromb Haemost* 1996 November; 76(5):786–90). Aprosulate is available from Lutipold Pharmaceuticals. In a preferred assay of the present invention, a sufficient amount of the aprosulate-containing reagent is combined with a sample for aprosulate to be present in the sample at about 10 mg/mL to about 50 mg/mL.

As used herein, the amino acid residues in a peptide are generally represented by standard 3 letter abbreviations known to those of skill in the art (e.g., Ala for alanine, Arg for arginine, Gly for glycine, Pro for proline; see page 60 of Dorland's Illustrated Medical Dictionary, 27th Ed., Philadelphia, W. B. Saunders Co., (1988)). Analogs of the preferred inhibitors that perform in accordance with the present invention are also included herein.

Preferred thrombin inhibitors of the present invention are direct thrombin inhibitors, and thus directly slow or inhibit the enzymatic conversion of fibrinogen to fibrin. Preferred direct thrombin inhibitors are competitive inhibitors that interact at the thrombin active site.

A preferred reagent comprises a thrombin inhibitor and thrombin at pre-optimized concentrations that can be used to determine fibrinogen in samples containing fibrinogen in concentrations found over the normal physiological range of clinical interest. Preferably, the reagent can be used to reliably determine fibrinogen concentrations in samples having between about 100 mg/dL and about 400 mg/dL fibrinogen. Lower and higher amounts of fibrinogen in samples can be determined using the assays and reagents of the present invention. It is believed that by optimizing the composition of the reagents of the present invention, fibrinogen levels can be determined ranging from about 0.5 mg/dL to about 2000 mg/dL, although determination of low and high ranges of fibrinogen concentrations may require varying reagent compositions for optimal results.

Further information on thrombin and thrombin inhibitors can be found in: Sturzebecher, Jorg et al., "Interactions of Thrombin with Benzamidine-based Inhibitors," *Biol. Chem. Hoppe-Seyler*, Vol. 373, pp. 491–496, July 1992; Dodt, Johanes et al., "Thrombin Inhibitors of Bloodsucking Animals," *Seminars In Thrombosis And Hemostasis*, Vol. 22, No. 2, pp. 203–208, 1996; Matsuo, Takefumi, et al., "Development of Argatroban, a Direct Thrombin Inhibitor, and Its Clinical Application," *Seminars In Thrombosis And Hemostasis*, Vol. 23, No. 6, pp. 517–522, 1997; Hursting, Marcie et al., "Novastan® (Brand of Argatroban): A Small Molecule, Direct Thrombin Inhibitor," *Seminars In Thrombosis And Hemostasis*, Vol. 23, No. 6, pp. 503–516, 1997; Okamoto, Shosuke, et al., "Enzyme Controlling Medicines: Introduction," *Seminars In Thrombosis And Hemostasis*, Vol. 23, No. 6, pp. 493–501, 1997; Preissner, Klaus, et al., "Thrombin Regulation by Physiological Inhibitors: The Role of Vitronectin," *Seminars In Thrombosis And Hemostasis*, Vol. 22, No. 2, pp. 165–172, 1997; Leung, Lawrence, "Application of Combinatorial Libraries and Protein Engineering to the Discovery of Novel Anti-Thrombotic Drugs," *Thrombosis and Haemostasis*, F. K. Schattauer Verlagsgesellschaft mbH (Stuttgart) 74(1) pp 373–376, 1995; Stone, Stuart, et al., "Thrombin Inhibitors As Antithrombotic Agents: The Importance Of Rapid Inhibition," *J. Enzyme Inhibition*, Vol 9, pp. 3–15, 1995; Shafer, Jules, "Cardiovascular Chemotherapy: anticoagulants," *Current Opinion in Chemical Biology*, Vol. 2, pp. 458–465, 1998; Maraganore, John, "Pre-clinical and Clinical Studies On Hirulog: A Potent and Specific Direct Thrombin Inhibitor," in The Design of Synthetic Inhibitors of Thrombin, Ed., G. Claeson, et al., New York, Plenum Press, pp. 227–236, 1993; Matsuo, Takefumi, et al., "Clinical Application of the Synthetic Thrombin Inhibitor, Argatroban (MD-805)" *Seminars In Thrombosis And Hemostasis*, Vol. 18, No. 2, pp. 155–160, 1992; Sanderson, P. et al., "Thrombin Inhibitor Design," *Current Medicinal Chemistry*, Vol. 5, pp. 289–304, 1998; Topol, Eric, "Evolution of Improved Antithrombotic and Antiplatelet Agents: Genesis of the Comparison of Abciximab Complications with Hirulog [and back-up Abciximab] Events Trial (CACHET)," *The American Journal of Cardiology*, Vol. 82(8B), pp. 63P–68P, Oct. 22, 1998; and White, Harvey, "Clinical Trials of Direct Thrombin Inhibitors In Acute Ischaemic Syndromes," *Thrombosis and Haemostasis*, F. K. Schattauer Verlagsgesellschaft mbH (Stuttgart) 78(1) pp 364–366, 1997.

Other Reagent Ingredients

In a preferred embodiment, the fibrinogen determination reagent of the present invention comprises thrombin and a thrombin inhibitor in a suitable buffer matrix, such as HEPES or PBS. A stabilizer, such as albumin, may also be present in the reagent. A substantially dry or anhydrous reagent can be formed using thrombin and a thrombin inhibitor in combination with other components designed to extend the shelf life and performance of the reagent. For example, a reagent for use in a test cartridge should be easy to apply to the cartridge flow path and/or reagent chamber, have a uniform consistency, be readily hydrated by and mixed into a sample, and be stable for a commercially reasonable amount of time. In some cases, bulking agents, such as sucrose, and wetting agents (e.g., surfactants) may be used to facilitate handling and optimize reagent performance.

Thrombin Inhibitor Evaluation

In order to determine which thrombin inhibitors provide optimal results with the assays of the present invention, samples containing varying concentrations of fibrinogen are contacted with a coagulating reagent comprising a particular thrombin inhibitor candidate or candidates and thrombin. While preferred thrombin inhibitors slow the rate of conversion of fibrinogen to fibrin, it is important that the total assay time not be so slow as to be impractical for routine use. Thus, it is preferred that sample fibrinogen conversion to fibrin should be substantially complete within less than about 300 seconds. However, samples containing different concentrations of fibrinogen within a range of interest must correlate to reliable and readily measurable differences in clotting time, particularly for the normal physiologic range of fibrinogen found in mammalian blood, and preferably human blood. Reagent compositions may require optimization for samples suspected of having low range or high range fibrinogen concentrations.

Determination of Suitable Thrombin Inhibitors for Use in the Present Invention In order to facilitate selection of optimal thrombin inhibitors, a series of experiments was performed utilizing standard thrombin solutions or dried reagents, which were contacted with standard samples having known fibrinogen concentrations and thrombin inhibitor candidates at varying but known concentrations. Qualitative criteria for determining preferred thrombin inhibitor candidates involved comparing the results of a standard sample having a known fibrinogen concentration containing an added thrombin inhibitor with an identical standard sample that did not contain added thrombin inhibitor. Quantitative criteria for determining the optimal amount of thrombin inhibitor required to perform an assay in accordance with the present invention involved preparation of multiple sets of fibrinogen standards, each set of standards containing a range of fibrinogen expected to be of interest. For example, 3 to 5 samples may comprise one set of fibrinogen standards in which the individual samples have differing fibrinogen concentrations ranging from 50 to 400 mg/dL. Each sample in a first set of standards is contacted with a particular thrombin inhibitor at a first known concentration and thrombin at a first concentration. Each sample in a second set of standards is contacted with the same thrombin inhibitor at a second known concentration and thrombin at the first concentration. The remaining sets are likewise contacted with thrombin inhibitor at a third, fourth, and/or fifth concentration and thrombin at the first concentration. The clotting time of the samples is compared to determine the optimal reagent composition.

Fibrinogen Assay

The fibrinogen concentration of a sample is inversely related to the sample's clotting time. In one embodiment, the clotting times of standards are determined after contact with a fixed amount of a standardized reagent of the present invention that contains thrombin and a thrombin inhibitor. The amount or concentration of fibrinogen in a sample suspected of containing fibrinogen can be determined by comparison of its clotting time after contact with the standardized reagent with the clotting times of the standards. As used herein, the expressions "determine fibrinogen" or "fibrinogen determination" refer to the determination of either total fibrinogen in a sample or the fibrinogen concentration of a sample. Likewise, "sample fibrinogen" can be used to refer to either the concentration or total amount of fibrinogen in a sample.

If the fibrinogen determination reagent does not contain a thrombin inhibitor, sample fibrinogen is determined by adding to the sample an inhibiting reagent containing a thrombin inhibitor in an effective amount prior to contacting the sample with an effective amount of the thrombin-containing fibrinogen determination reagent to cause clotting. The clotting time of samples is compared with that of standards to determine fibrinogen.

In a preferred embodiment of the present invention, the fibrinogen assay of the present invention is optimized for use of a particular thrombin modulator in order to determine sample fibrinogen concentrations that are less than, meet, or exceed the normal mammalian physiological concentration range of fibrinogen. For example, using a constant concentration of thrombin and a constant concentration of a particular thrombin inhibitor, clotting times are determined for a series of standard samples containing varying amounts of fibrinogen.

Assays of samples suspected of having high range fibrinogen concentrations may yield more accurate and precise results using a first reagent containing a particular thrombin inhibitor and thrombin combination, while assays of samples suspected of having low range fibrinogen concentrations may use a second reagent which may either utilize a different amount of thrombin inhibitor and/or thrombin, or the second reagent may utilize a different thrombin inhibitor.

Wet Assay

The optimization experiments and fibrinogen assay described above can be performed in a wet assay, in which the sample of interest is combined in a vessel with a thrombin inhibitor and thrombin. A sensor is used to detect clotting or a predetermined degree of clotting, and a timer is used to measure the time to achieve the predetermined degree of clotting. A commercially available fibrometer may be used to determine when a predetermined degree of clotting is reached (a BBL Fibrometer is suitable; more information on fibrometer equipment is available from BD Biosciences, 1 Becton Drive, Franklin Lakes, N.J., USA). The fibrinogen concentration of a sample is determined by measuring the time to reach a predetermined degree of clotting after contacting the sample with a known amount of a known inhibitor and thrombin and comparing the clotting time with that of standards that were contacted with the same amount of the same inhibitor and thrombin.

Figure 1:
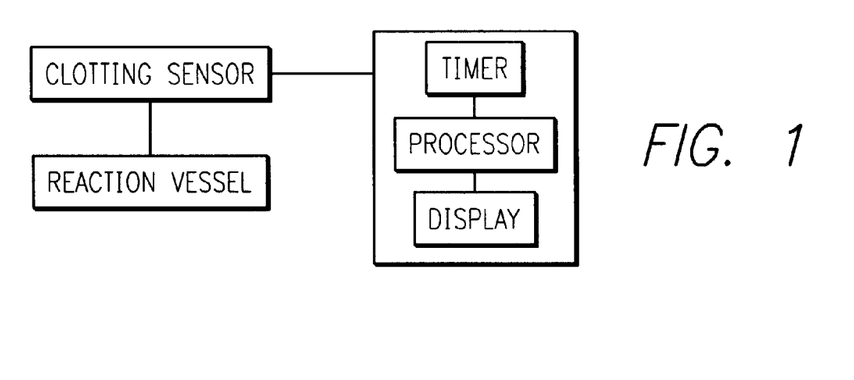
FIG. 1 is a box diagram of a device comprising a reaction vessel, a clotting sensor, a timer, a processor and a display.

With reference to FIG. 1, a box diagram of a wet assay device is illustrated. A reaction vessel is utilized for contacting a sample suspected of containing fibrinogen with at least one reagent that causes conversion of fibrinogen to fibrin, thus causing clotting. The preferred reagent is an optimized reagent of the present invention, comprising a thrombin inhibitor and thrombin. A sensor detects clotting, or a predetermined degree of clotting, and a timer measures the time to reach a predetermined degree of clotting. In a preferred embodiment, a processor converts clotting time to fibrinogen concentration, which is output to a display. The display may be electronic or may be a printer. The clotting time and other parameters may also be displayed (i.e., patient, doctor name, etc.).

Cartridge Assay

In a preferred embodiment, the reagents of the present invention are used in a modified device for determining clotting times, such as those described in U.S. Pat. Nos. 4,756,884 and 5,039,617, which describe an integrated device containing a pre-dispensed, dry reagent in a capillary track that can be used to measure the clotting time of blood samples. The entire disclosure of these two patents is incorporated herein by reference as if reproduced in full below. The assignee of the present invention currently markets a system under the designation CoaguChek™ Pro and CoaguChek™ Plus (available from Roche Diagnostics Corporation, Indianapolis, Ind.), the disposable cartridge of which was modified for use with the assay of the present invention. The cartridge-reagent system employed in the CoaguChek™ Plus system uses a blood sample to solubilize a reagent within the cartridge and to move the reagent with the blood through the cartridge tracks during the coagulation reaction. Clotting time is determined by a detector that detects the rate of flow of blood cells (e.g., red blood cells) or blood cell surrogates (e.g., latex beads or particles) through the capillary. In an alternative embodiment, the reagent in the cartridge may be used wet.

A method, reagent and test cartridge for determining clotting time is described in provisional application ser. No. 60/152,450, filed Sep. 3, 1999, entitled Method, Reagent And Test Cartridge For Determining Clotting Time, and its co-pending continuation-in-part, Ser. No. 09/678,950, filed Oct. 3, 2000, which are assigned to the assignee of the present invention. The entire disclosure of said applications are incorporated herein by reference as if reproduced in full below. In a preferred embodiment, the reagents of the present invention are applied to the capillary of a test cartridge using the same techniques described in said application. The present invention also contemplates the determination of fibrinogen in blood plasma and synthetic blood, wherein blood cell surrogates are mixed with the sample prior to passage through the capillary.

Figure 2A:
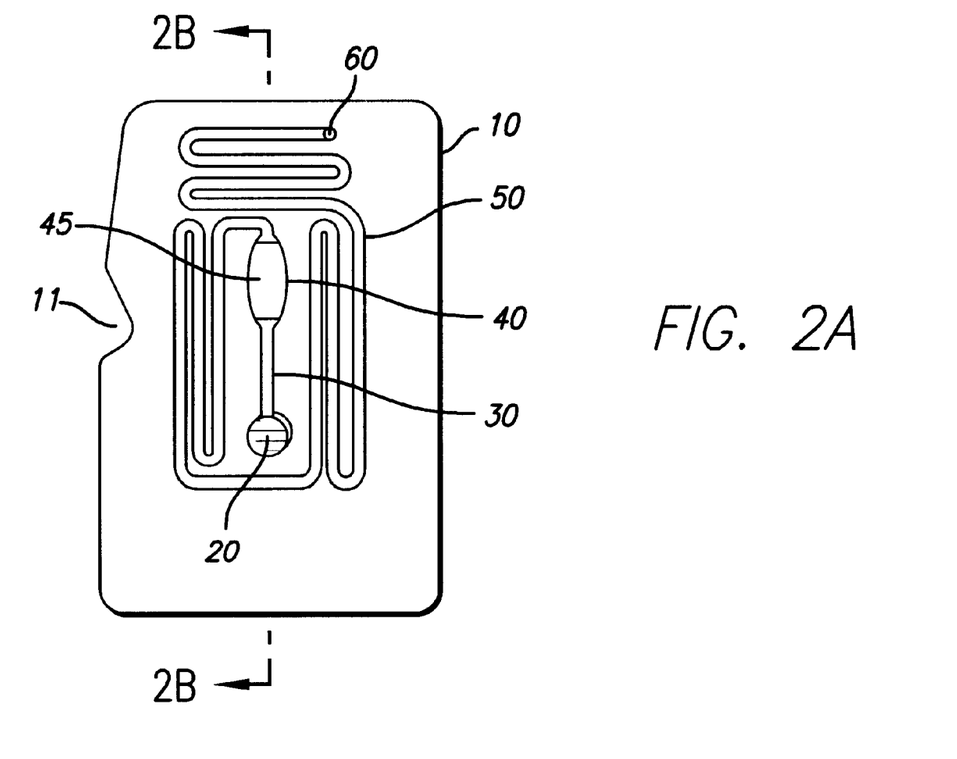
FIGS. 2A and 2B are plan and cross-sectional views of the test cartridge of the present invention.

A preferred test cartridge in accordance with the present invention is shown in FIG. 2A. The cartridge comprises a housing that may be configured for use with an instrument for assay determination, such as a CoaguChek™ Plus clotting time determination device (available from Roche Diagnostics Corporation, Indianapolis, Ind., USA). For example, notch 11 in housing 10 is provided to allow retention of the device (e.g., by a spring-activated catch) in the instrument in which the analysis will be carried out. The housing is constructed so as to ensure sufficient mechanical stability to withstand mechanical handling and provide for the necessary characteristics for flow of the assay medium and detection of the detectable signal. Entry port 20 is provided for access of a blood sample to the internal capillary of the device. A first capillary passage 30 transports blood to reagent chamber 40 containing reagent 45. In the embodiment shown, housing 10 is provided with clear surfaces at the location of capillary 30 in order that this section of the capillary track can be utilized to measure movement (and cession of movement) of sample (e.g., blood) using a speckle-pattern detector. The sample, now mixed with reagent 45, exits chamber 40 and enters capillary flow unit 50, which connects chamber 40 to vent 60. Capillary flow unit 50 is a long, convoluted capillary pathway that provides sufficient path length for flow to be sustained for a time sufficient to measure the clotting time.

Figure 2B:
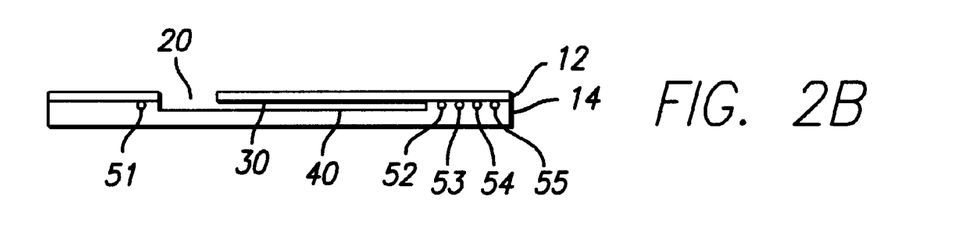

A cross sectional view of the embodiment shown in FIG. 2A is set forth in FIG. 2B. This cross sectional view is taken along the lines B—B of FIG. 2A. The construction of housing 10 from two plates, 12 and 14, is evident in this cross-sectional view. Plate 12 is essentially a flat plate that has been welded onto plate 14, which contains grooves and other depressions in its upper surface that will form the internal chambers and capillaries of the device. The two plastic pieces 12 and 14 have been welded together after being properly aligned (e.g., placed in register). "Registration" is used here in the sense of referring to proper alignment of the depressions present in the surfaces of the two pieces that are used to form the internal chambers and capillaries. Proper registration can be aided by injection molding the two pieces to provide projections on one piece that fit into holes or depressions (other than capillary- or chamber-forming depressions) in the second piece.

A single convoluted depression used to form capillary channels and chambers is present in the surface of plate 12. The cross-sectional view shown in FIG. 2 cuts through the depression at six separate locations, some of which (51, 52, 53, 54, and 55) are part of the capillary flow unit 50, while the remaining location will result in the formation of the larger initiation capillary 30 and reaction chamber 40 when plates 12 and 14 are welded together.

The cartridge-reagent system employed in the CoaguChek™ Plus system uses a blood sample to solubilize a reagent within the cartridge and to move the reagent with the blood through the cartridge tracks during the coagulation activation reaction. In an alternative embodiment, the reagent in the cartridge may be used wet. It is also anticipated that the reagent may be applied to a three dimensional matrix, which may increase surface area, such as paper, gel, sponges and microcapsules. Thus, in an alternative embodiment, a matrix material, such as a gel may contain the reagent in a wet form. In a preferred embodiment, the cartridge is disposed of after use.

When the reagent is supplied within test cartridges, the reagent may be present in either a diffusive or non-diffusive relationship to the surface of the cartridge, that is, adhered, absorbed, adsorbed or covalently-linked so that the reagent may become dissolved in the fluid or may remain fixed to the surface. Where the reagents are diffusively bound (non-covalently and weakly bound), a variety of situations can be accommodated. One situation is where the liquid front dissolves the reagent completely, so that the liquid front receives a high concentration of the reagent and most of the reaction occurs at the liquid front. A second situation would be with an excess of a reagent of limited solubility. In this situation, the reagent may be present in the liquid medium at a substantially uniform concentration. A third situation is to have a deficiency of a reagent of limited solubility, so that only the early portion of the fluid will have a relatively constant reagent concentration. It is preferred to disperse a liquid containing the dissolved reagents onto the surface of a reagent chamber. The liquid is spread over the chamber surface and dried under low humidity air. Thus, in a preferred embodiment, the reagent is substantially dehydrated. Various wetting and spreading agents may be utilized to optimize reaction conditions.

In order to assure the reproducibility of distribution, various techniques may be employed for introducing the reagent into the chamber. Where the cartridge is produced as two parts which fit together, the reagent may be sprayed, painted, introduced into the chamber as a liquid, lyophilized or evaporated, adsorbed, covalently conjugated, or the like. The active reagent may be combined with various stabilizers, excipients, buffers or other additives involved with the reaction. For example, HEPES is a preferred buffer, and albumin is preferably added as a thrombin stabilizer.

To enhance mixing, various mechanical or ultrasonic means may be employed to agitate the sample and reagents, where the mixing means may be internal or external. Vibrators, ultrasonic transducers, magnetic rods or other mechanical mixing means, flow disrupters, mixing baffles or barriers, flow directors, or the like, may be employed. The particular manner in which agitation is provided, if provided, will vary widely depending upon the degree of agitation needed, the design of the cartridge, and the like.

The reagent need not be coated or bound to the surface of the cartridge, but may be provided as a soluble sponge or gel or alternatively, absorbed onto an insoluble sponge, membrane, paper (e.g., filter paper) or gel which is introduced into the reaction unit. In this manner the fluid may pass through the foam structure dissolving the reagent so as to form the reaction mixture.

The reagent may be provided in liquid form in microcapsules. The liquid reagent could be released from the microcapsules by applying pressure to the walls of the reaction unit, resulting in breaking of the microcapsules and releasing the liquid reagent.

The clotting time determination device and cartridge described above is used to determine the clotting time of a sample suspected of containing fibrinogen by adding the sample to entry port 20. Clotting time is determined by detecting a reduction in the rate of flow of a sample through said capillary. Clotting time is generally associated with the stoppage of flow or when flow has substantially stopped. As used herein, clotting time indicates the time it takes for the rate of flow to drop below a predetermined rate in a capillary type device (this is generally when flow rate drops below the detection level of the device used), or the amount of time it takes for a predetermined degree of clotting to occur in a wet chemical analysis. In a preferred embodiment, the clotting time of a sample passing through a cartridge is correlated with sample fibrinogen concentration by use of standardized cartridges. Standardized cartridges are fabricated based upon prior testing of standard reagent cartridges with samples containing a range of fibrinogen concentrations. In a preferred embodiment, the clotting time device will utilize a standard cartridge, and provide the fibrinogen concentration readout automatically based upon the clotting time of the sample. In a preferred embodiment, the device includes a processor for converting sample clotting time to sample fibrinogen concentration.

Multifunctional Assay Device

Figure 3:
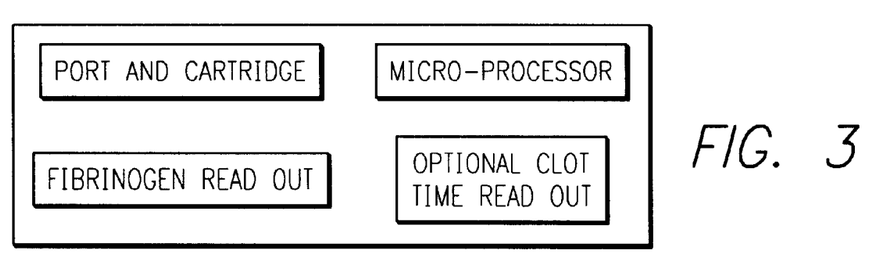
FIG. 3 is a box diagram of a device incorporating the cartridge of the present invention in relation to a processor and a display.

With reference to FIG. 3, a box diagram of a device incorporating a cartridge of the present invention in relation to a processor and readout device is illustrated. The processor converts clotting time to fibrinogen concentration, and preferably includes a memory for storing data from standards and samples. An optional feature is a read out for clotting time. The clotting time readout may also be provided by the same display that provides fibrinogen concentration. Preferably, a flow detector is in operable connection with the processor that converts sample clotting time to fibrinogen concentration, which in turn is in operable connection with a read-out device that provides the device operator with the fibrinogen concentration, and optionally also provides clotting time. Suitable circuitry and devices that can be modified or programmed for converting a first numerical result (i.e., clotting time) to a second numerical result (i.e., fibrinogen concentration) are widely available.

In an embodiment, a suitable microprocessor and software/firmware to correlate the clotting time of a sample with its fibrinogen concentration are provided in a modified CoaguChek™ Plus Device, along with a readout device or display that provides sample fibrinogen concentration. The display may also provide clotting time and other parameters and information, such as patient identifier, doctor name, and insurance information. Appropriate data storage and retrieval software is preferably provided therewith to permit data on standards and samples to be stored and analyzed. Thus, a multi-functional device is provided in one embodiment that may be used for fibrinogen assays as well as for other clotting time dependent assays.

In order to prepare standardized cartridges, which can be used to link clotting time to sample fibrinogen concentration, it was necessary to first prepare and test various reagents comprising thrombin and thrombin inhibitor candidates to determine optimal cartridge reagents. This was initially done using the wet assay with a fibrometer described above to determine suitable thrombin inhibitor candidates prior to preparing and testing cartridges containing dried reagent.

EXAMPLES

The following examples are provided by way of illustration and explanation and as such are not to be viewed as limiting the scope of the present invention. Further, various methods may be used to link sample clotting time to a fibrinogen concentration. One embodiment utilizes the clotting time of standards to generate a graph of clotting time versus fibrinogen concentration, against which the clotting time of a sample may be compared. In an alternative embodiment, the clotting time of standards containing varying fibrinogen concentrations may be subjected to statistical analysis to generate an algorithm for directly calculating a sample's fibrinogen concentration from its clotting time. In a preferred embodiment, a clotting time device may be preprogrammed with an algorithm, which is based on a particular sample size mixed with a fixed amount of standardized clotting reagent, to automatically yield a sample's fibrinogen concentration from its clotting time (i.e., time required to reach a predetermined degree of clotting).

In an alternative embodiment, a data storage device and processor may be utilized to automatically compare the clotting times of a series of standards with that of a sample containing an unknown amount of fibrinogen. The processor preferably includes statistical programming to calculate algorithms for different standards and sample types.

Example 1

Wet Screening Assay for Suitable Thrombin Inhibitors

Testing of Dextran Sulfate

A screening assay was developed for determining whether or not a particular thrombin inhibitor candidate would be useful in the assay of the present invention. An initial investigation was undertaken to determine if a sulfated polysaccharide, such as dextran sulfate, would sufficiently inhibit thrombin activity in samples containing the normal physiological range of fibrinogen concentrations.

Materials and Methods: A phosphate buffered saline (PBS)-albumin solution was formed as follows:

| INGREDIENT | CONCENTRATION | SOURCE |
| --- | --- | --- |
| NaCl | 0.145M | Aldrich 22351-4 |
| KCl | 2.7 mM | Sigma P4504 |
| $Na_2HPO_4$ | 16.9 mM | Aldrich 22199-6 |
| $NaH_2PO_4$ | 2.5 mM | Aldrich 22352-2 |
| Albumin | 4.0 g/dL | Sigma A7030 |
| PH | 7 | |

The PBS-albumin solution was used to form standard dextran sulfate (D.S.), thrombin, and fibrinogen working solutions as follows:
1) 0.5 mg/mL dextran sulfate ("D.S.") working solution. Dextran sulfate (@10,000 MW) was obtained from Sigma®;
2) 100 U/mL thrombin working solution; thrombin was obtained from Calbiochem (605206—human plasma, or 605157—bovine); and
3) fibrinogen working solutions having fibrinogen concentrations ranging from between 6 and 24 mg/mL fibrinogen; fibrinogen was obtained from Calbiochem (341578).

Screening Assay Procedure Using Fibrometer: A BBL Fibrometer was utilized to determine clotting times of test solutions. Test solutions were formed by adding the following components in the following order:
1. 200 µL D.S. working solution,
2. 50 µL thrombin working solution,
3. 50 µL fibrinogen working solution.

Immediately upon addition of the third component (i.e., the fibrinogen working solution), the fibrometer was activated, resulting in the probe being released into the vessel containing the reaction solution. The probe was agitated until sufficient resistance to motion was reached corresponding to a predetermined degree of clotting. A display indicated time from activation of the probe until the predetermined degree of clotting was reached.

The dilution of working solutions containing 6 to 24 mg/mL fibrinogen in the reaction mixtures resulted in solutions having fibrinogen concentrations ranging from 100 to 400 mg/dL, which spans the normal physiological concentration range of fibrinogen.

Results For Varying Concentrations of Fibrinogen: The Table below compares solution fibrinogen concentration with clotting times after contact with a reagent containing dextran sulfate (10,000 Da) and thrombin.

| Final Assay Concentration Of Fibrinogen (mg/dL) | Clot Time (seconds) |
| --- | --- |
| 100 | 22.8 |
| 200 | 11.8 |
| 250 | 9.8 |
| 400 | 1.2 |

If no dextran sulfate was present in the assay reaction mixture, the clot time was about 0.6 seconds (time when the probe plunged into the assay cup).

Thus, dextran sulfate was found to be a useful thrombin inhibitor reagent in the fibrinogen assay of the present invention. Normal mammalian whole blood and blood plasma, such as human blood and blood plasma, is believed to have substantially the same clotting attributes as the test samples above. Thus, the assay of the present invention, using a reagent comprising predetermined or optimized levels of thrombin and a suitable thrombin inhibitor can be used to analyze fibrinogen in undiluted blood and undiluted blood plasma.

In a preferred embodiment, using a reagent comprising thrombin and 10,000 Da dextran sulfate as a thrombin inhibitor, samples are combined with a sufficient amount of the reagent to have a thrombin concentration of between about 1 U/mL and about 100 U/mL and a dextran sulfate concentration between about 0.1 mg/mL and about 20.0 mg/mL.

Example 2

Screening of Benzamidine as a Thrombin Inhibitor with Fibrometer Wet Assay

Using the method of Example 1, 15 mg/mL benzamidine (Sigma B6506) in the PBS-albumin solution (final concentration) was contacted with samples containing varying amounts of fibrinogen. The results are presented in tabular form below:

| Sample Fibrinogen Concentration (mg/dL) | Clotting Time (average, in seconds), n = 2 |
| --- | --- |
| 100 | 242 |
| 200 | 139 |
| 400 | 93 |

By varying the benzamidine concentration in the resulting reaction mixture, it was found to be most effective when present in the sample at an amount between about 5 and about 50 mg/mL.

Other thrombin inhibitor candidates were tested with the fibrometer "wet assay" technique of Example 1. Those found to be effective for use in the present invention include, dextran sulfate (50,000 Da—Dextralip 50), and antipain. Preferably the Dextralip 50 is present in the sample reaction mixture in an amount ranging from about 0.75 to about 5 mg/mL, and antipain is present in an amount ranging from about 0.5 to about 1 mg/mL.

Example 3

Testing Of New Assay Cartridge

An assay cartridge as described above was constructed in which the reagent chamber was coated with a dried reagent containing thrombin in a HEPES buffer matrix. Liquid samples containing latex beads as blood cell surrogates and various levels of fibrinogen were introduced into the cartridge contained within a CoaguChek™ Plus device. Just prior to introducing a sample into the device, the particular thrombin modulator being tested was added to the sample. A variety of thrombin modulators were tested in this manner.

A HEPES Base solution, pH=7.4, was formed from the following ingredients:

| INGREDIENT | CONCEN-TRATION | SOURCE |
|---|---|---|
| HEPES Buffer | 200 mM | Calbiochem 391338 |
| Sodium Chloride | 50 mM | Aldrich 22351-4 |
| Albumin from bovine serum (stabilizer) | 0.2 g/dL | Sigma A7030 |
| Triton X-100 (wetting agent) | 0.02 g/dL | Boehringer Mannheim 789-704 |
| Sucrose (bulking agent) | 16 g/dL | Sigma S8501 |
| Bromophenol blue | 0.2 g/dL | Sigma B6131 |
| Sodium Azide | 0.3 g/dL | Aldrich 19,993-1 |

A thrombin solution was formed by adding thrombin (Calbiochem 605157 bovine) to the HEPES Base solution, the resulting concentration being 67 units/mL thrombin.

A 10% solution by weight of polystyrene spheres with a mean diameter of 3.27 μm (Bang Laboratories P0032700) was utilized as a blood cell surrogate for plasma or synthetic blood solutions "plastic sphere solution").

Testing Protocol

Test cartridges were prepared by applying 3 microliters of the thrombin solution thereto and drying the solution. For each sample, a fresh "thrombin" cartridge was utilized.

For each sample, a thrombin cartridge was placed into a Coaguchek® Plus device. Test samples were prepared by combining 35 μL of the fibrinogen working solution (see Example 1), 5 μL of a solution containing the inhibitor being evaluated (See Thrombin Inhibitor table below), and 7 μL of the plastic sphere solution. The test sample was applied to the inlet port of the cartridge, and sample clotting time measured. When no inhibitor was present, clotting time was under 10 seconds. Thus, effective inhibitors would increase clotting time above 10 seconds, but preferably not above 300 seconds.

The following Table identifies non-limiting examples of various inhibitors found to be effective using the foregoing procedure:

| THROMBIN INHIBITOR | CONCENTRATION IN REAGENT |
|---|---|
| Dextran Sulfate-10,000 Da | 2, 8.5 and 21 mg/mL |
| Dextran Sulfate-5,000 Da | 5 mg/mL |
| Dextran Sulfate-50,000 Da (Dextralip ® 50) | 5 mg/mL |
| Benzamidine | 4 and 11 mg/mL |
| Gly-Gly-Arg | 0.85 and 1.3 mg/mL |
| Gly-Pro-Arg | 0.2 and 0.85 mg/mL |
| Caffeine | 0.85, 1.6 and 8.5 mg/mL |
| Polyvinylsulfate | 0.25, 0.5 and 5 mg/mL |
| Polyanetholesulfate | 0.5 and 5 mg/mL |
| Aprosulate | 21 and 43 mg/mL |

All of the foregoing inhibitors slowed the sample clotting time to above 10 seconds and below 300 seconds for samples having fibrinogen concentrations between 50 and 400 mg/dL, and allowed clotting time to be correlated with fibrinogen concentration.

Example 4

Measuring the Clotting Times of Samples with Varying Fibrinogen Concentrations but Fixed Sample Thrombin Inhibitor Concentration on Cartridges with Standard Dried Thrombin Reagent Cartridges containing the dried thrombin reagent were utilized for the following experiments. Standard solutions were prepared in accordance with Example 3, except the thrombin inhibitor concentration was fixed, and the fibrinogen concentrations varied.

The following Table provides clotting times for samples containing a fixed amount of dextran sulfate (10,000 Da) but varying amounts of fibrinogen after standard sized samples were applied to the inlet port of thrombin containing cartridges.

| CLOTTING TIME OF FIBRINOGEN SOLUTIONS CONTAINING 21 MG/ML DEXTRAN SULFATE (10,000 DA) ||
|---|---|
| Fibrinogen Concentration (mg/mL) In Combined Assay Solution | Clotting Time (seconds) After Application To Inlet Port Of Cartridge Containing Thrombin Reagent |
| 100 | 157.5 |
| 102 | 81.9 |
| 204 | 28.6 |

The following Table provides clotting times for samples containing a fixed amount of Gly-Pro-Arg peptide but varying amounts of fibrinogen after standard sized samples were applied to the inlet port of thrombin containing cartridges.

| CLOTTING TIME OF FIBRINOGEN SOLUTIONS CONTAINING 0.85 mg/mL GLY-PRO-ARG PEPTIDE ||
|---|---|
| Fibrinogen Concentration (mg/mL) In Combined Assay Solution | Clotting Time (seconds) After Application To Inlet Port Of Cartridge Containing Thrombin Reagent |
| 100 | 239.6 |
| 102 | 44.1 |
| 204 | 9.9 |

The following Table provides clotting times for samples containing a fixed amount of caffeine but varying amounts of fibrinogen after standard sized samples were applied to the inlet port of thrombin containing cartridges.

| CLOTTING TIME OF FIBRINOGEN SOLUTIONS CONTAINING 1.6 mg/mL CAFFEINE ||
|---|---|
| Fibrinogen Concentration (mg/mL) In Combined Assay Solution | Clotting Time (seconds) After Application To Inlet Port Of Cartridge Containing Thrombin Reagent |
| 100 | 88.8 |
| 200 | 30.0 |
| 400 | 24.8 |

The following Table provides clotting times for samples containing a fixed amount of aprosulate but varying amounts of fibrinogen after standard sized samples were applied to the inlet port of thrombin containing cartridges.

| CLOTTING TIME OF FIBRINOGEN SOLUTIONS CONTAINING 43 mg/mL APROSULATE | |
|---|---|
| Fibrinogen Concentration (mg/mL) In Combined Assay Solution | Clotting Time (seconds) After Application To Inlet Port Of Cartridge Containing Thrombin Reagent |
| 76 | 149.1 |
| 153 | 85.5 |
| 306 | 21.4 |

Example 5

Measuring the Clotting Times of Samples with Varying Fibrinogen Concentrations On Cartridges With Standard Dried Reagent Comprising Thrombin Inhibitor and Thrombin Additional cartridges were prepared in which specific inhibitors were combined with the thrombin solution, the thrombin inhibitor/thrombin solution deposited in the cartridge, and dried. A thrombin-dextran sulfate (TDS) reagent was prepared by combining the HEPES base solution described above with thrombin and dextran sulfate to yield a reagent solution containing 67 units/mL thrombin and 57 mg/mL dextran sulfate (10,000 Da). The TDS reagent (3 microliters) was applied to cartridges and dried. Fibrinogen test samples for these cartridges comprised 40 µL of the fibrinogen working solution combined with 7 µL of the plastic sphere solution. The clotting time of the fibrinogen test samples in the TDS cartridges is provided in tabular form below.

| CLOTTING TIME OF FIBRINOGEN SOLUTIONS IN CARTRIDGE CONTAINING DEXTRAN SULFATE AND THROMBIN | |
|---|---|
| Fibrinogen Concentration (mg/mL) In Combined Assay Solution | Clotting Time (seconds) After Application To Inlet Port Of Cartridge |
| 99 | 69.6 |
| 198 | 40.0 |
| 396 | 26.7 |

Additional cartridges were prepared in which aprosulate was used as the specific inhibitor. A thrombin-aprosulate (TA) reagent was prepared by combining the HEPES base solution described above with thrombin and aprosulate to yield a reagent solution containing 67 units/mL thrombin and 20 10 g/dL aprosulate. The TA reagent (3 microliters) was applied to cartridges and dried. Fibrinogen test samples for these cartridges comprised 40 µL of the fibrinogen working solution combined with 7 µL of the plastic sphere solution. The clotting time of the fibrinogen test samples in the TA cartridges is provided in tabular form below.

| CLOTTING TIME OF FIBRINOGEN SOLUTIONS IN CARTRIDGE CONTAINING APROSULATE AND THROMBIN | |
|---|---|
| Fibrinogen Concentration (mg/mL) In Combined Assay Solution | Average Clotting Time (seconds) After Application To Inlet Port Of Cartridge (n = 2) |
| 25.5 | 275 |
| 102 | 134 |
| 204 | 41 |
| 408 | 24 |

Optimum sensitivity over the widest range of fibrinogen concentrations can be achieved by optimizing the assay conditions for the specific thrombin modulator. This can be done without undue experimentation by one of ordinary skill in the art by following the procedures set forth herein and by modifying the various parameters. The optimal reagent may depend on whether the fibrometer or cartridge device is used.

Non-limiting examples of thrombin inhibitors found to be effective in experiments with one or both of the two assays above (i.e., wet and cartridge) include dextran sulfate (5,000–50,000 MW), the peptides Gly-Pro-Ala and Gly-Gly-Arg; caffeine; polyanetholesulfate, polyvinylsulfate, bis-lactobionic acid (aprosulate), benzamidine, and antipain. The determination of which analogs of these compounds and what other compounds may be useful with the present invention can be performed using the methods set forth above.

Thus, these various inhibitors may be used with whole blood samples and blood plasma samples in the same fashion as the working solutions of the Examples.

Cartridges for One-step Procedure for Determining Fibrinogen in Whole Blood

Example 5 demonstrates that undiluted whole blood, rather than synthetic blood with latex particles as blood cell surrogates, can be introduced into the cartridges of the present invention in a single-step assay to determine fibrinogen therein. Undiluted blood plasma, after combination with latex particles or another blood cell surrogate (as a first step), can be introduced into the sample cartridges in a two-step assay to determine fibrinogen therein.

In an alternative embodiment, blood plasma can be analyzed in a single-step assay by combining a blood cell surrogate, latex beads for example, with the reagent in the cartridge reagent chamber. The blood plasma will mix with the reagent/particle mix and pass through the capillary. In order to optimize the assay, the detector may be moved distally of the reagent chamber.

Thus, new reagents, devices, and assays are provided for the determination of fibrinogen in physiological samples. Use of the test cartridge of the present invention preferably requires no sample dilution and no or minimal addition of reagent prior to insertion of the sample into the cartridge. For example, undiluted whole blood can be directly added to the cartridge sample well, and a readout of fibrinogen concentration directly provided, while the fibrinogen in undiluted blood plasma can be determined in the same type of cartridge by addition of a blood cell surrogate.

The preceding description of preferred embodiments should be viewed as exemplary and not as limiting. For example, while preferred embodiments utilize undiluted blood, diluted samples can be used in the same manner.

Other methods of linking clotting time to fibrinogen concentration may be used, for example, standards additions, wherein the clotting time of samples suspected of containing fibrinogen are determined following the addition of known but varying amounts of fibrinogen to like-sized aliquots of sample. Further, while tests of particular thrombin inhibitors have been illustrated herein, it is to be understood that other compounds having similar activity are encompassed within the scope of the invention.

What is claimed is:

1. A method for determining fibrinogen in a sample suspected of comprising fibrinogen, comprising contacting a sample suspected of comprising fibrinogen with at least one reagent comprising a thrombin inhibitor and thrombin, and determining the clotting time, whereby the concentration of fibrinogen in the sample is inversely related to the clotting time.

2. The method of claim 1, wherein the sample is blood or plasma.

3. The method of claim 2, wherein the sample is undiluted.

4. The method of claim 1, wherein the thrombin inhibitor and the thrombin are combined in a single reagent.

5. The method of claim 1, wherein the thrombin inhibitor is added to the sample before the thrombin is added.

6. The method of claim 1, wherein the sample is contacted with sufficient thrombin so that the sample comprises between about 1 U/mL and about 100 U/mL thrombin.

7. The method of claim 1, wherein said thrombin inhibitor comprises at least one compound selected from the group consisting of a sulfated polysaccharide, a peptide with thrombin inhibiting properties, a xanthine, a polyanetholsulfate; a polyvinylsulfate, bis-lactobionic acid, a benzamidine, a serine protease inhibitor, hirudin, hirulog, bivalirudin, and argatroban.

8. The method of claim 7, wherein said sulfated polysaccharide is dextran sulfate.

9. The method of claim 8, wherein said dextran sulfate has a molecular weight between about 5,000 Da and about 50,000 Da.

10. The method of claim 8, wherein said sample is contacted with sufficient dextran sulfate to comprise between about 0.01 mg/mL and about 25 mg/mL dextran sulfate.

11. The method of claim 7, wherein said xanthine is caffeine.

12. The method of claim 11, wherein said sample is contacted with sufficient caffeine to comprise between about 0.85 and about 8.5 mg/mL caffeine.

13. The method of claim 7, wherein said benzamidine is a cyclic amide of 4-amidinophenylalanine.

14. The method of claim 13, wherein said cyclic amide of 4-amidinophenylalanine is Nα-(β-naphthylsulfonylglycyl)-4-amidinophenylalanine piperidide.

15. The method of claim 14, wherein said sample is contacted with sufficient benzamidine to comprise between about 4 and about 11 mg/mL benzamidine.

16. The method of claim 7, wherein said serine protease inhibitor is antipain, and wherein said sample is contacted with sufficient antipain to comprise between about 0.5 mg/mL and about 1.0 mg/mL antipain.

17. The method of claim 7, wherein said peptide is at least one compound selected from the group comprised of Gly-Gly-Arg and Gly-Pro-Ala.

18. The method of claim 17, wherein said sample is contacted with sufficient peptide to comprise between about 0.85 and about 1.3 mg/mL Gly-Gly-Arg when Gly-Gly-Arg is the peptide and and between about 0.2 and about 0.85 mg/mL Gly-Pro-Ala when Gly-Pro-Ala is the peptide.

19. The method of claim 1, wherein said thrombin inhibitor is bislactobionic acid.

20. The method of claim 1, wherein said thrombin inhibitor is aprosulate, and said sample is contacted with sufficient aprosulate to comprise between about 10 and about 50 mg/mL aprosulate.

21. The method of claim 1, wherein the clotting time is applied to a predefined algorithm to determine fibrinogen.

22. The method of claim 1, wherein the clotting time is compared against a set of predetermined times, each of said predetermined times being correlated to a fibrinogen concentration, wherein fibrinogen in the sample may be determined.

23. The method of claim 1, wherein the clotting time of the sample is determined by detecting a reduction in the flow of the sample through a chamber.

24. The method of claim 1, wherein the thrombin and thrombin inhibitor are contained within a chamber of a test cartridge;

the sample is added to the chamber and mixed with the thrombin and thrombin inhibitor;

the test cartridge includes a capillary through which the sample and reagent are caused to flow; and wherein the clotting time is determined by detecting reduction in the rate of flow of said sample through said capillary.

25. The method of claim 24, further comprising the step of converting the clotting time of the sample to a fibrinogen concentration.

26. The method of claim 1, wherein the amount of thrombin and thrombin inhibitor combined with the sample are selected so as to produce clotting times less than about three hundred seconds for samples containing between about 100 mg/dL fibrinogen and about 400 mg/dL fibrinogen, and permit correlation of detectable differences in clotting times of different samples with clinically significant differences in fibrinogen concentration.

27. The method of claim 24, wherein said sample is blood plasma, and wherein a blood cell surrogate is added to said sample.

28. A reagent for use in determining fibrinogen in a sample suspected of containing fibrinogen, said reagent comprising a thrombin inhibitor and thrombin, wherein when a sufficient amount of said reagent is combined with a sample having a fibrinogen concentration ranging from about 0.5 mg/dL to about 2000 mg/dL the time for the sample to reach a predetermined degree of clotting is less than about 300 seconds and the concentration of fibrinogen in the sample can be correlated with the time required to achieve the predetermined degree of clotting.

29. The reagent of claim 28, wherein the sample is whole blood or blood plasma.

30. The reagent of claim 28, wherein the sample is undiluted whole blood or undiluted blood plasma.

31. The reagent of claim 28, wherein said thrombin inhibitor comprises at least one compound selected from the group consisting of a sulfated polysaccharide, a peptide with thrombin inhibiting properties, a xanthine, a polyanetholsulfate; a polyvinylsulfate, bis-lactobionic acid, a benzamidine, a serine protease inhibitor, hirudin, hirulog, bivalirudin, and argatroban.

32. The reagent of claim 31, wherein said sulfated polysaccharide is dextran sulfate with a molecular weight between about 5,000 Da and about 50,000 Da.

33. The reagent of claim 32, wherein when sufficient reagent is combined with a sample containing fibrinogen ranging from about 0.5 mg/dL to about 2000 mg/dL to cause a predetermined degree of clotting within less than about 300 seconds, the sample will comprise between about 0.01 mg/mL and about 25 mg/mL dextran sulfate.

34. The reagent of claim 31, wherein said xanthine is caffeine.

35. The reagent of claim 34, wherein when sufficient reagent is combined with a sample containing fibrinogen ranging from about 0.5 mg/dL to about 2000 mg/dL to cause a predetermined degree of clotting within less than about 300 seconds, the sample will comprise between about 0.85 mg/mL and about 8.5 mg/mL caffeine.

36. The reagent of claim 31, wherein said benzamidine is a cyclic amide of 4-amidinophenylalanine.

37. The reagent of claim 36, wherein said cyclic amide of 4-amidinophenylalanine is Nα-(β-naphthylsulfonylglycyl)-4-amidinophenylalanine piperidide.

38. The reagent of claim 36, wherein when sufficient reagent is combined with a sample containing fibrinogen ranging from about 0.5 mg/dL to about 2000 mg/dL to cause a predetermined degree of clotting within less than about 300 seconds, the sample will comprise between about 4 mg/mL and about 11 mg/mL benzamidine.

39. The reagent of claim 31, wherein said serine protease inhibitor is antipain.

40. The reagent of claim 39, wherein when sufficient reagent is combined with a sample containing fibrinogen ranging from about 0.5 mg/dL to about 2000 mg/dL to cause a predetermined degree of clotting within less than about 300 seconds, the sample will comprise between about 0.5 mg/mL and about 1.0 mg/mL antipain.

41. The reagent of claim 31, wherein said peptide is at least one compound selected from the group comprised of Gly-Gly-Arg and Gly-Pro-Ala.

42. The reagent of claim 41, wherein when sufficient reagent is combined with a sample containing fibrinogen ranging from about 0.5 mg/dL to about 2000 mg/dL to cause a predetermined degree of clotting within less than about 300 seconds, the sample will comprise between about 0.85 mg/mL and about 1.3 mg/mL Gly-Gly-Arg when said peptide is Gly-Gly-Arg and between about 0.2 mg/mL and about 0.85 mg/mL Gly-Pro-Ala when said peptide is Gly-Pro-Ala.

43. The reagent of claim 28, wherein said thrombin inhibitor is bis-lactobionic acid.

44. The reagent of claim 28, wherein said thrombin inhibitor is aprosulate, wherein when sufficient reagent is combined with a sample containing fibrinogen ranging from about 0.5 mg/dL to about 2000 mg/dL to cause a predetermined degree of clotting within less than about 300 seconds, the sample will comprise between about 10 mg/mL and about 50 mg/mL aprosulate.

45. The reagent of claim 28, wherein said reagent is a dry reagent that is hydrated by the sample.

46. The reagent of claim 28, wherein when a sufficient amount of said reagent is combined with a sample having a fibrinogen concentration ranging from about 100 mg/dL to about 400 mg/dL the time for the sample to reach a predetermined degree of clotting is less than about 300 seconds and the concentration of fibrinogen in the sample can be correlated with the time required to achieve the predetermined degree of clotting.

47. The reagent of claim 28, further comprising a blood cell surrogate.

48. The reagent of claim 28, further comprising a stabilizer and a buffer.

49. A test cartridge for use in determining fibrinogen in a sample, comprising a housing containing an inlet port, a chamber and an exit port wherein said inlet port, chamber and exit port are present in a continuous capillary pathway; and the reagent of claim 28 in said capillary pathway.

50. The test cartridge of claim 49, wherein said reagent is dry and can be hydrated by a sample.

51. A test cartridge for use in determining fibrinogen in a sample containing a thrombin inhibitor, comprising:

a housing containing an inlet port, a chamber unit and an exit port, said inlet port, chamber unit and exit port are present in a continuous capillary pathway; and a reagent in said capillary pathway, said reagent comprising thrombin.

52. A device for use in determining fibrinogen in a sample, comprising:

the test cartridge of claim 49 or 51; and a flow detector to determine the clotting time of the sample.

53. The device of claim 52, further comprising a processor to convert the clotting time of the sample into a fibrinogen concentration.

54. The device of claim 53, further comprising a printer for printing the fibrinogen concentration.

55. The device of claim 54, wherein the printer also prints the clotting time.

56. A device for use in determining fibrinogen in a sample suspected of containing fibrinogen, comprising:

a vessel for contacting a sample suspected of containing fibrinogen with a reagent that causes conversion of fibrinogen to fibrin thereby causing clotting, a sensor for detecting a predetermined degree of clotting, a timer for determining the amount of time for a predetermined degree of clotting to be reached, a processor that converts clotting time to the amount of fibrinogen in a sample, and a display that can report the amount of fibrinogen in a sample.

57. The device of claim 56, further comprising a reagent that causes conversion of fibrinogen to fibrin, wherein said reagent comprises thrombin and a thrombin inhibitor.

* * * * *